(12) United States Patent
Llacer (10) Patent No.: US 6,411,675 B1
(45) Date of Patent: Jun. 25, 2002

(54) STOCHASTIC METHOD FOR OPTIMIZATION OF RADIATION THERAPY PLANNING

(76) Inventor: Jorge Llacer, 130 Forest Hill Dr., Los Gatos, CA (US) 95032

( * ) Notice: Subject to any disclaimer, the term of this patent is extended or adjusted under 35 U.S.C. 154(b) by 53 days.

(21) Appl. No.: 09/712,405

(22) Filed: Nov. 13, 2000

(51) Int. Cl.$^7$ .................................................. A61B 5/01
(52) U.S. Cl. ........................................ 378/65; 378/64
(58) Field of Search .............................. 378/64, 65, 68

(56) References Cited

U.S. PATENT DOCUMENTS

| | | | | |
|---|---|---|---|---|
| 5,418,827 A | * | 5/1995 | Deasy et al. | 378/65 |
| 5,602,892 A | | 2/1997 | Llacer | |
| 5,740,225 A | * | 4/1998 | Nabatame | 378/65 |
| 5,859,891 A | * | 1/1999 | Hibbard | 378/62 |
| 6,038,283 A | | 3/2000 | Carol et al. | |

OTHER PUBLICATIONS

J. Llacer, "Inverse radiation treatment planning using the Dynamically Penalized Likelihood method", Med. Phys., 24, (11) pp 1751–1764, 1997.

T. Bortfeld, et al. "Methods of image reconstruction from projections applied to conformation radiotherapy", Pys. Med. Biol., vol. 35, No. 10, 1423–1434, 1990.

T. Bortfeld, et al. "Three–dimensional solution to the inverse problem in conformation radiotherapy", Advanced Radiation Therapy Tumor Response Monitoring and Treatment Planning, Breit Ed., Springer, pp 503–508, 1992.

T. Bortfeld, et al. "Decomposition of pencil beam kernels for fast dose calculations in three–dimensional treatment planning", Med. Phys. 20 (2), Pt. 1, pp 311–318, 1993.

T. Bortfeld, et al. "Clinically relevant intensity modulation optimization using physical criteria", Proceedings of the XII$^{th}$ ICCR, Leavitt & Starkschall, eds., Springer, pp 1–4, 1997.

S.V. Spirou and C–S. Chui, "A gradient inverse planning algorithm with dose–volume constraints", Med. Phys. 25(3), pp 321–333, 1998.

S. Webb, "Optimizing radiation therapy inverse treatment planning using the simulated annealing technique", Int. Journal of Imaging Systems and Tech., vol. 6, pp 71–79, 1995.

* cited by examiner

Primary Examiner—David V. Bruce (57) ABSTRACT

A method of optimization for fluence modulated radiation therapy or fluence modulated radiation surgery based on a new Adaptive Simulated Annealing (ASA) method. The cost function of the ASA method is analytic and, therefore, has first partial derivatives with respect to the fluences to be estimated that can be calculated rapidly. That cost function has terms for the organs at risk that change dynamically as the iterative calculations proceed towards an optimization. The resulting dose volume distributions for the organs at risk are near the distributions specified by the user, while the doses to the planning treatment volume voxels are as close to the desired dose as physically possible, consistent with the conditions established for the organs at risk.

16 Claims, 8 Drawing Sheets

STOCHASTIC METHOD FOR OPTIMIZATION OF RADIATION THERAPY PLANNING

FEDERALLY SPONSORED RESEARCH AND DEVELOPMENT

The work that lead to the present invention was funded, in part, by a Small Business Innovation Research grant of the National Cancer Institute, No. CA76808-03.

BACKGROUND OF THE INVENTION

1. Field of the Invention

The invention relates to radiation therapy planning for the treatment of tumors or for stereotactic radiosurgery and more particularly to the optimization of the radiation dose delivered to a patient by inverse treatment planning.

2. Description of the Background Art

The delivery of radiation for the treatment of tumors or obliteration of other abnormalities in human patients has undergone important changes in the last few years. The most important change has been the use of fine pencil beams of radiation of fixed intensity that can be scanned in a manner similar to a raster, remaining in each position of the scan for different lengths of time. With groups of pencil beams directed to the tumor or abnormality from different angles around the body, it is possible to deliver a radiation dose distribution that is effective in the treatment of the tumor or abnormality while sparing organs or tissues that are in the path of the radiation beams. That technology is known as Fluence Modulated Radiation Treatment (FMRT) or Fluence Modulated Radiation Surgery (FMRS). For historical reasons, it is also commonly known as Intensity Modulated Radiation Treatment/Surgery (IMRT/S) although the latter terminology is misleading since it implies modulated beam intensities.

The problem of therapy planning for FMRT/S is a difficult one: the fluences of a large number of pencil beams from many angles have to be calculated so that the sum of all their effects results in a uniform dose to the volume that contains the tumor or abnormality. Excessive dose to some portions of that volume can result in medical complications and under-dosing a region can lead to poor tumor control or recurrence. At the same time, the calculated fluences must fulfill some restrictive requirements to the radiation dose that is allowable in the different sensitive tissues traversed by the beams. The requirements placed by a therapist may be medically desirable but, to a smaller or larger extent, will be inconsistent with the physical laws that govern the absorption of radiation by the different tissues in the patient. The calculation of beam fluences, then, requires a methodology that allows for those inconsistencies and still delivers a set of beam flux results that achieve the most important of the desired results, as defined by the therapist. The process of obtaining that set of results is usually termed "optimization". The volume that includes the tumor or other abnormalities to be treated is normally termed "Planning Treatment Volume", or PTV. There can be more than one PTV in a treatment plan, but, without loss of generality, this document will refer to a PTV in the singular. Similarly, the volume that includes sensitive tissues or organs is normally termed "Organ at Risk", or OAR. There can be more than one OAR, but the term will be used in the singular, without loss of generality, except when giving specific examples with multiple OAR's.

Optimization is invariably carried out by maximizing or minimizing a target or cost function incorporating the requirements and limitations placed by the therapist on the solution of the problem. Once a target or cost function has been defined, an algorithm is called upon to find the values of the beam fluence variables that will maximize or minimize that function, as the case may require.

Current art in optimization for FMRT/S can be divided into technologies that use:

a) a mathematically derived iterative formula to maximize or minimize the target or cost function. Those methods need an analytic target or cost function, so that it has explicit first partial derivatives with respect to the beam fluence variables.

b) a stochastic method that repeatedly tries maximizing or minimizing a target or cost function by testing whether a small change in the fluence of a randomly selected beam results in a change of that function in the desired direction.

Current art for the two types of technologies can be summarized as:

a1) using a Dynamically Penalized Likelihood target function which maximizes the likelihood that the resulting beam fluence values will yield the desired dose to the PTV, subject to a maximum dose specified for the OAR (see U.S. Pat. No. 5,602,892, J. Llacer, "Method for Optimization of Radiation Therapy Planning", Feb. 11, 1997; and J. Llacer, "Inverse radiation treatment planning using the Dynamically Penalized Likelihood method", Med. Phys., 24, (11) pp 1751–1764, 1997).

a2) using a quadratic cost function which is to be minimized, with additional quadratic penalty functions imposed to apply restrictions. A gradient method speeded up by scaling the gradient with the inverse of the diagonal elements of the Hessian matrix is used for that minimization. It allows for specifying the maximum dose to the OAR and also the fraction of the OAR volume that is allowed to receive more than a certain dose (see T. Bortfeld, J. Bürkelbach, R. Boesecke and W. Schlegel, "Methods of image reconstruction from projections applied to conformation radiotherapy", Pys. Med. Biol., 1990, Vol 35, No. 10, 1423–1434; T. Bortfeld, J. Bürkelbach and W. Schlegel, "Three-dimensional solution to the inverse problem in conformation radiotherapy", Advanced Radiation Therapy Tumor Response Monitoring and Treatment Planning, Breit Ed., Springer, pp 503–508, 1992; T. Bortfeld, W. Schlegel and B. Rhein, "Decomposition of pencil beam kernels for fast dose calculations in three-dimensional treatment planning", Med. Phys. 20 (2), Pt. 1, pp 311–318, 1993; and T. Bortfeld, J. Stein and K. Preiser, "Clinically relevant intensity modulation optimization using physical criteria", Proceedings of the XII$^{th}$ International Conference on the Use of Computers in Radiation Therapy (ICCR), Leavitt & Starkschall, eds., Springer, pp 1–4, 1997).

a3) using a quadratic cost function with constraints that limit the space of the allowable solutions to those that are non-negative (there cannot be negative beam fluences) and lead to doses to the OAR that are not above a maximum and/or result in no more than a specified fraction of the OAR volume receiving more than a certain dose. A modified form of the Conjugate Gradient method is used for minimization of the cost function (see S. V. Spirou and C-S. Chui, "A gradient inverse planning algorithm with dose-volume constraints", Med. Phys. 25 (3), pp 321–333, 1998).

b1) using the Simulated Annealing technique, a stochastic method, to minimize a variety of proposed cost functions, including some possibly important biological functions like Tumor Control Probability and Normal Tissue Complication Probability (see S. Webb, "Optimizing radiation therapy inverse treatment planning using the simulated annealing technique", Int. Journal of Imaging Systems and Tech., Vol. 6, pp 71–79, 1995, which summarizes the extensive work over many years by that author and co-workers) and b2) using non-analytic cost functions that describe the fractions of PTV and OAR volumes that are to receive no more or less than a certain range of doses. The minimization of those cost functions is carried out by the simulated annealing method, (see U.S. Pat. No. 6,038,283, M. P. Carol, R. C. Campbell, B. Curran, R. W. Huber and R. V. Nash, "Planning method and apparatus for radiation dosimetry", Mar. 14, 2000).

The above methods are either in use at several institutions in the U.S. and elsewhere or being prepared for inclusion in Radiation Therapy Planning commercial software packages by several Companies.

An advantage attributed to the stochastic method of U.S. Pat. No. 6,038,283 is that it allows the therapist to define cost functions that prescribe the fractions of PTV and OAR volumes that are to receive no more or less than a certain range of doses. In order to provide that advantage, that method has to use non-analytic cost functions without explicit first partial derivatives. Testing whether a small change in the fluence of a randomly selected beam will result in an increase or decrease of the cost function involves complex calculations that slow down the optimization considerably. The number of times that those complex calculations have to be carried out for a prostate cancer case, for example, may be $5 \times 10^5$.

Short optimization calculation times are important in the clinic. Even with substantial experience, a therapist may have to recalculate a therapy plan several times, each time with a somewhat different set of PTV and OAR restrictions, until a satisfactory compromise optimization has been found.

Because of the frequent inconsistencies imposed by Physics between the doses that a therapist would want to prescribe for a PTV and an OAR, it is important not to over-constrain the problem. What is needed is an implementation of the Simulated Annealing method that allows the therapist to specify the fractions of the OAR volume that are to receive no more than a certain range of doses but allows the optimization algorithm to do its best for the PTV automatically. Furthermore, if the method uses an analytic cost function with partial derivatives that can be calculated rapidly, the therapist will have the ability to explore several possible optimizations within a clinically practical computation time and select the one that best suits the medical requirements of the patient.

SUMMARY OF THE INVENTION

The present invention is a new Adaptive Simulated Annealing (ASA) method of optimization. It uses the stochastic method of Simulated Annealing, in conjunction with dynamic characteristics related to the Dynamically Penalized Likelihood method of U.S. Pat. No. 5,602,892, to minimize an adaptive analytic cost function, with desired values of dose for each of the voxels of the OAR selected by a novel methodology. It allows the therapist to specify the fraction of OAR volumes that are to receive no more than a certain range of doses, while yielding a dose in each of the PTV voxels that is as close as physically possible to the desired dose.

Specifically the invention includes a method and apparatus for solving a numerical optimization problem that yields pencil beam fluences that will result in the optimum treatment plan using a predetermined set of pencil beams.

The preferred method and apparatus for solving the numerical optimization problem comprises a computer running a new ASA iterative algorithm. Taking into consideration the desired dose in all the PTV voxels, the range of maximum doses desired for different fractions of the OAR volume and the energy deposited per unit fluence into the patient's tissues by all the selected pencil beams, the new ASA algorithm finds the beam fluences that minimize the cost function:

$$B(a) = \sum_{i \in D} w_i \Phi(h_i^{(k)}, d_i) + \sum_{\substack{i \in S \\ (h_i^{(k)} - s_i) > 0}} \beta_i \Theta(h_i^{(k)}, s_i)$$

wherein
a=vector of pencil beam fluences
$h_i^{(k)}$ is the dose received by voxel i at iteration k,
$d_i$=desired dose in voxel i of the PTV,
D=the region that includes all the voxels of the PTV,
$s_i$=desired dose in voxel i of the OAR,
S=the region that includes all the voxels of the OAR,
$\Phi(\ )$=an analytic function of the dose received by voxel i in the PTV at iteration k and of the desired dose for the same voxel,
$\Theta(\ )$=an analytic function of the dose received by voxel i in the OAR at iteration k and of the desired dose for the same voxel,
$w_i$=weights that determine how closely the minimization of $\Phi(\ )$ has to be carried out for voxel i in the PTV, and
$\beta_i$=weights that determine how closely the minimization of $\Theta(\ )$ has to be carried out for voxel i in the OAR.

The dose received by a voxel i at iteration k is defined by $$h_i^{(k)} = \sum_j F_{ij} a_j^{(k)}$$

wherein:
$a_j^{(k)}$=fluence for the $j^{th}$ pencil beam at iteration k and
$F_{ij}$=element of the dose matrix F, giving the dose received in voxel i per unit fluence of pencil beam j.

An iteration consists of an attempt to minimize the cost function by increasing or decreasing the value of one randomly selected pencil beam fluence by a small amount.

Since the therapist only prescribes a range of maximum doses to be received by specific fractions of the OAR volume but cannot define which specific voxels are to receive a specific maximum dose, the desired doses $s_i$ are calculated by a new procedure which takes into consideration the doses $h_i^{(k)}$, for i∈S, after an optimization of the PTV only and the therapist's specification.

The cost function has a second condition for inclusion of a particular OAR voxel i into the second summation. That condition is $(h_i^{(k)} - s_i) > 0$, which means that if a voxel receives a higher dose than desired in iteration k, it will be included in the summation. If a voxel already receives a lower dose than desired, that voxel does not enter into the computation of the cost function, or its derivatives, during iteration k. The number of terms in the cost function, then, changes dynamically and results in the "adaptive" nature of the new algorithm. The use of dynamic changes in the cost function of Simulated Annealing is another novelty of the ASA method.

An alternative method and apparatus for solving the numerical optimization problem comprises a computer running a form of the ASA iterative algorithm in which the analytic functions $\Phi(\ )$ and $\Phi(\ )$ are the quadratic forms $$\Phi(h_i^{(k)}, d_i) = (h_i^{(k)} - d_i)^2$$

and $$\Theta(h_i^{(k)}, s_i) = (h_i^{(k)} - d_i)^2.$$

OBJECTS AND ADVANTAGES

Accordingly, several objects and advantages of the invention are:

A primary object of the invention is to provide optimization of dose delivery in FMRT/FMRS procedures.

Another object of the invention is to provide radiation doses in the OAR that match or are less than the range of radiation doses specified by a therapist for the different voxels of the OAR.

Another object of the invention is to match radiation doses in the PTV to the desired dose in that volume as well as physical laws allow.

Another object of the invention is to provide optimization that allows the therapist to explore the space of available solutions in a clinically useful time.

An advantage of this invention is that it can provide optimizations for FMRT/S without over-constraining the PTV specifications.

Another advantage of this invention is that it can use analytic cost functions and respond to a detailed specification of which fractions of the OAR volume should receive no more than a certain dose range.

Yet another advantage of this invention is that optimizations can be obtained in relatively short computation times.

Other objects, advantages and novel features will be set forth in the following portions of the specification, wherein the detailed description is for the purpose of fully disclosing the preferred embodiment of the invention, without placing limitations thereon.

BRIEF DESCRIPTION OF THE DRAWINGS

The accompanying drawings, which are incorporated into and form a part of the specification, illustrate the preferred embodiment of the invention and, together with the description, serve to explain the principles of the invention. The drawings are only to illustrate the preferred embodiment of the invention and are not to be construed as limiting the invention.

DESCRIPTION OF THE PREFERRED EMBODIMENT

Figure 1:
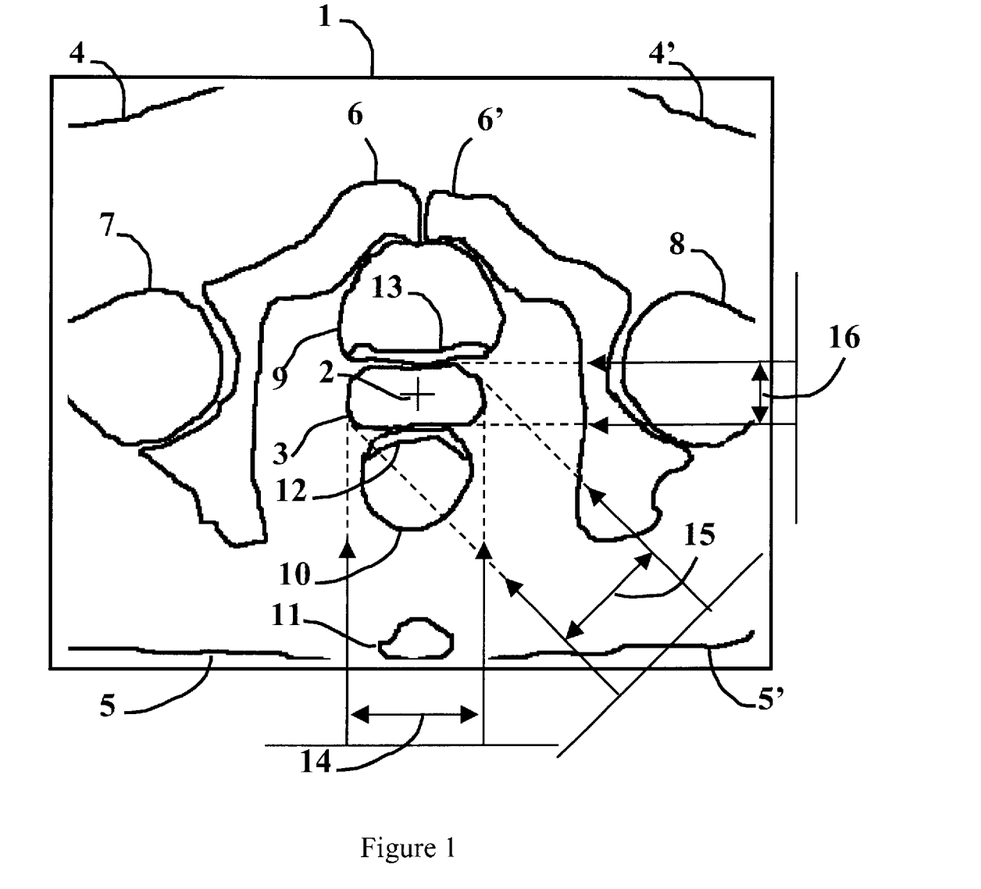
FIG. 1 is a simplified description of the environment in which the ASA algorithm is to perform its function. It shows a tracing by hand on a computer screen of the principal tissues and organs of one plane of a prostate cancer patient's anatomy, as obtained from a Computerized Tomography scan. It also shows the width of the range of radiation pencil beams for three of the many possible treatment angles that can be used around the patient.

Graphical and numerical information on the important organs and tissues for a treatment plan are usually placed in a computer memory in the form of a stack of consecutive Computerized Tomography (CT) and/or Magnetic Resonance (MR) scans. The therapist will outline the PTV and the OAR's in each of the planes in the stack by hand, using a mouse and, if possible, some automated means. In FIG. 1, one such planes 1 has been outlined by hand by tracing a CT scan on a computer screen with a mouse. It corresponds to a patient with a prostate cancer. The plane shown corresponds to approximately the three-dimensional center 2 of the prostate 3. The anterior body contours 4 and 4' and the posterior body contours 5 and 5' are shown. The outlines of the pelvic bones 6 and 6', of the right head of the femur 7 and of the left head of the femur 8 are also shown. The bladder 9 is anterior to the prostate 2 and in close contact. Likewise, the colon 10 is posterior to the prostate 2 and in close contact. The outline of the coccyx 11 is also shown. The prostate 3 is the PTV, where a uniform high dose of radiation is to be delivered. The anterior wall of the colon 12 and the posterior wall of the bladder 13 are designated OAR's, since those portions of the colon 10 and of the bladder 9 are considerably more at risk because of proximity to the prostate 3.

The radiation pencil beams are directed to the PTV (the prostate 3) from different angles around the patient. As examples, FIG. 1 shows the total width covered by pencil beams that will hit the prostate from an angle of 0° 14, of 45° 15, and of 90° 16. For the case of the 0° angle, for example, there may be 25 pencil beams side-by-side covering a prostate 3 width of approximately 5 cm. The number of pencil beams varies with the angle around the patient, so as to cover fully the PTV. It is usually not possible to deliver the wanted dose to the PTV from only those angles that do not traverse the OAR's, like the 90° angle. The damage that would be done to normal tissues in the path of the few beams that could be used would make such a plan unacceptable.

For a therapy plan covering all the different planes that contain prostate tissue, as many as 2000 pencil beam fluences may have to be optimized. That is the function of ASA algorithm given the complete anatomical information, the physical characteristics of the radiation pencil beams chosen by the therapist, the dose desired for the PTV and the limits on dose that can be tolerated by the OAR's.

The doses desired for or resulting from a treatment plan can best described by a Dose Volume Distribution (DVD), also called Cumulative Dose Volume Histogram (CDVH). The simpler Dose Volume Histogram (DVH) is a histogram of the number of voxels in a particular patient tissue volume that receive a certain radiation dose. The DVD is then an integral of the DVH starting from the high dose end, normalized to 100% volume.

Figure 2:
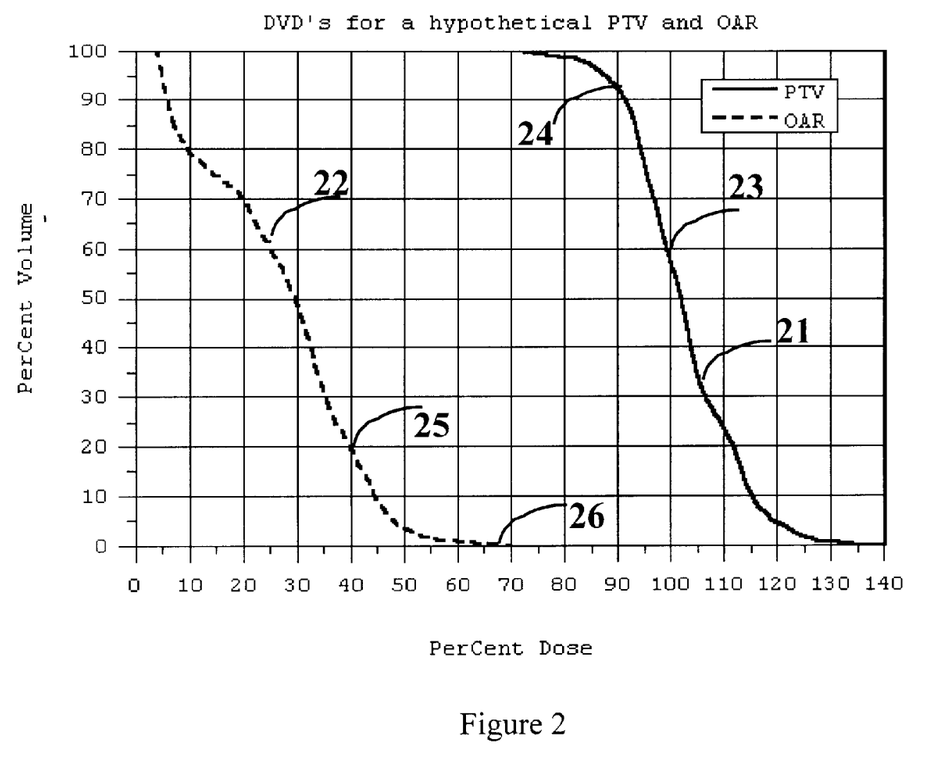
FIG. 2 is a Dose Volume Distribution (DVD) for a hypothetical Planning Treatment Volume (PTV) and one Organ at Risk (OAR), used to illustrate the characteristics of such distributions.

FIG. 2 shows two DVD curves, for a PTV 21 and an OAR 22, in a hypothetical case. To read this type of graph, consider the PTV curve 21 and notice that it crosses a PerCent Dose of 100 at 60% volume, at point 23. This indicates that 60% of the PTV volume is receiving more than 100 units of radiation. Similarly, the point at 24 indicates that 92% of the PTV voxels are receiving more than 90% dose, or what is the same, that 8% of the PTV volume is receiving less than 90% dose. The latter interpretation of point 24 is most important, since usually under-dosing a PTV can result in poor tumor control or recurrence. For the OAR curve 22, the point at 25 indicates that 20% of its volume is receiving more than 40 units of dose. The point at 26 indicates that the maximum dose received by the OAR is 68%. The section of the OAR curve 22 between points 25 and 26 may be most important because some OAR tissues may be able to tolerate a relatively high dose as long as only a small fraction of its volume is involved. A therapist may want to specify several points in an OAR like that of curve 22, based on the clinical experience with a particular type of tumor or abnormality and the involved OARs.

Figure 3:
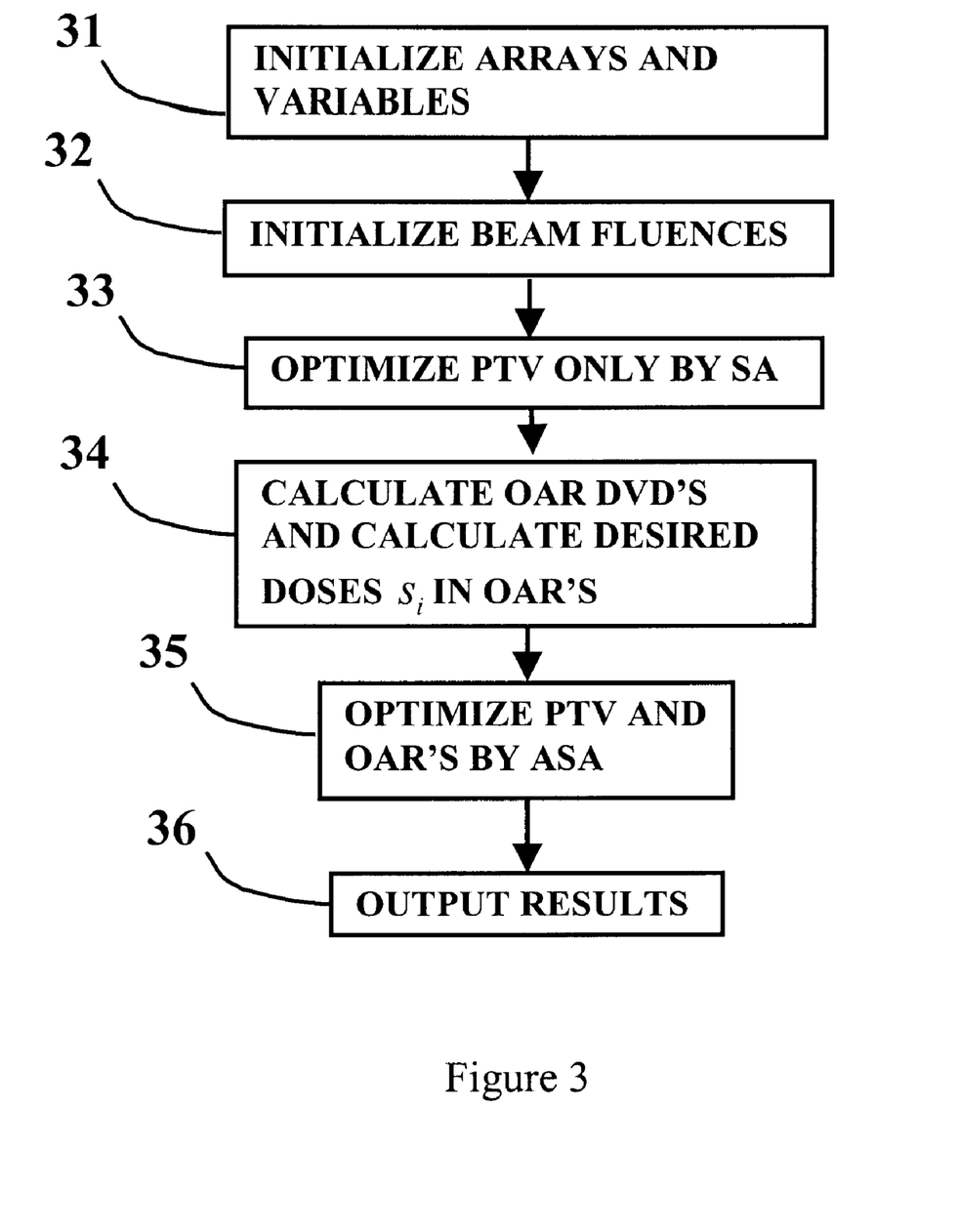
FIG. 3 is a diagram that describes the overall flow and processing of information in the ASA algorithm.

FIG. 3 shows the overall flow and processing of information in the ASA optimization algorithm. The most important initialization carried out at 31 is the placement into a computer memory of all the elements of the "dose matrix" F. An element $F_{ij}$ corresponds to the dose received in voxel i per unit fluence of pencil beam j. The dose matrix is calculated taking into consideration all the physical information about the patient anatomy, the physical characteristics of the chosen pencil beams and the radiation absorption by the patient's tissues and it is, therefore, a major part of the optimization process. The dose matrix has to be calculated for each patient and beam configuration and is normally calculated by a therapy planning system, of which there are a number of commercially available units. The units in which dose and beam fluence are calculated depend on the choice made by the designers and/or users of the planning system and are irrelevant to the optimization process, as long the choice of units is used consistently by that system. It is to be noted that each column of the dose matrix corresponds to one pencil beam to be used in the therapy and each row corresponds to one voxel in the PTV or OAR.

The desired dose in the PTV and the restrictions placed on the OAR doses by the therapist are also initialized in 31. Information about which voxels (dose matrix rows) corresponds to the PTV or OAR, the maximum number of iterations for the subsequent processes and parameters related to determination of convergence are also initialized in 31.

The beam fluences are the variables to be estimated by the optimization process. Initial values for those fluences have to be calculated so that the optimization has a reasonable starting point. This is carried out in 32.

Before carrying out the fall ASA optimization, it is necessary to do a preliminary optimization of the PTV only, neglecting the OARS. This is done at 33. The OAR DVDs resulting from 33 are needed in 34, which is described next.

The therapist specifies the desired restrictions to be placed on the OAR doses by placing two or more points in the DVD for each OAR. Those points indicate which fraction of the OAR volume should receive no more than a certain range of doses, but does not specify precisely which OAR voxels are going to fall in each volume fraction. In order to be able to use analytic functions as cost functions, it is necessary to assign a desired dose $s_i$ to each OAR voxel i and insure that the resulting desired dose distribution matches the therapist's points in the corresponding OARS. This is carried out by the operations in 34.

At this point all the necessary conditions for an ASA optimization have been satisfied and 35 carries out that optimization.

At 36, the optimized pencil beam fluences are made available to the therapy planning system that will verify that those fluences will actually deliver the desired dose distributions in a patient. The verification is normally done by a computer program that has been certified by the Federal Drug Administration.

Figure 4:
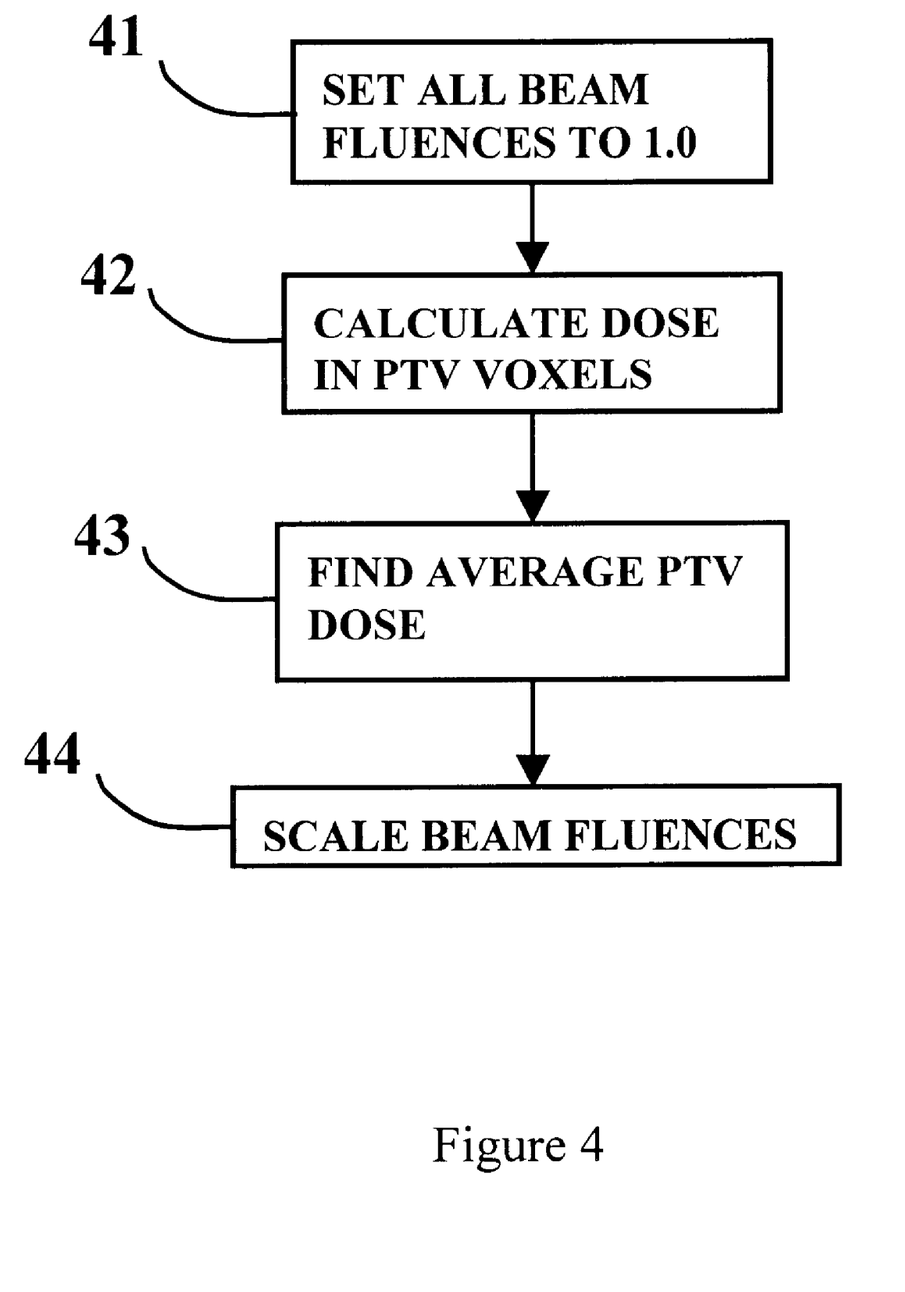
FIG. 4 is a diagram that describes the flow and processing of information in the INITIALIZE BEAM FLUENCES step in FIG. 3.

FIG. 4 describes the process of initializing the beam fluences for an optimization. In 41 all beam fluences are set to 1.0. In 42, a computer calculates the dose that would be received by the PTV if those beam fluences were actually delivered to a patient. This is done by the matrix product $$d_{0i} = \sum_j F_{ij} a_j \text{ with } a_j = 1.0 \text{ for all } j, i \in D, \text{ or}$$

$$d_{0i} = \sum_j F_{ij}.$$

In 43 the average PTV dose is obtained as $$\bar{d}_0 = \frac{1}{N_i} \sum_i d_{0i}$$

wherein $N_i$ is the number of voxels in the PTV.

Finally, in 44, a scale factor γ is obtained by the quotient $$\gamma = \frac{\text{Desired dose in the } PTV \text{ voxels}}{\bar{d}_0}$$

and all the beam fluences are initialized to the value γ. This initialization leads to a PTV dose that is not necessarily uniform but it has the right order of magnitude for the units of dose and fluence in use for the particular optimization.

Figure 5:
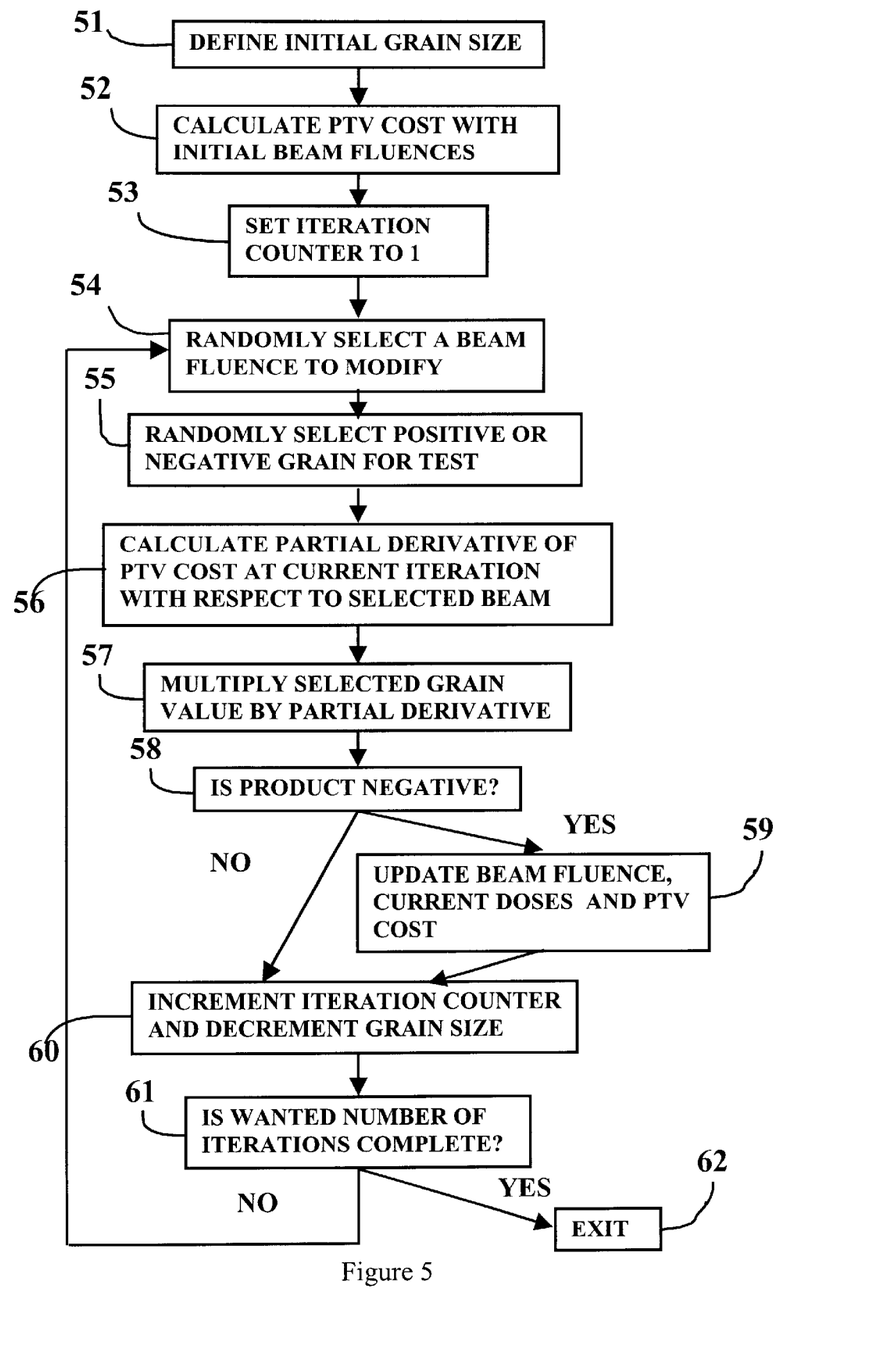
FIG. 5 is a diagram that describes the flow and processing of information in the OPTIMIZE PTV ONLY BY SA step in FIG. 3.

FIG. 5 describes the processing and information flow in a PTV only optimization, disregarding the OARs, that is needed as a preamble to the full ASA optimization. It is carried out by an efficient form of the standard Simulated Annealing method.

A "grain" $\Delta a^{(k)}$ is defined as a small change in beam fluence $as_j^{(k)}$ at iteration k. The grain has a magnitude and a sign. It is used to test whether a change in $a_j^{(k)}$ by $\Delta a^{(k)}$, for some j, leads to lowering the value of the cost function or not. The initial magnitude of the grain, $\Delta a^{(0)}$, is taken in 51 as a fixed fraction of the scale factor γ, defined in 44 as the initial value $a_j^{(0)}$ for all j. A fraction of the order of 0.02 is useful.

In 52, the analytic cost function Φ( ) for the PTV, which has been decided upon by the therapy planning system designer and coded into the optimization program, is called upon to calculate the cost of a solution with the initial values of beam fluences γ. For example, if the PTV analytic function is the quadratic $$\Phi(h_i^{(k)}, d_i) = (h_i^{(k)} - d_i),$$

the right hand side corresponds to the square of the differences between dose received at iteration k and the desired dose for each voxel i of the PTV.

One "iteration" has been defined as one test with a change of one grain in one randomly selected beam fluence. The test may lead to acceptance of that change if leading to a lower cost or rejection otherwise. In 53 the iteration counter is set to 1.

In 54, a random number generator is used to select one of the beams j for a test. In 55, a positive or negative sign for the grain is chosen at random for the test corresponding to the current iteration.

In 56, the first partial derivative of the PTV cost function with respect to the beam being tested is calculated. For example, if the PTV cost function is the above quadratic and the beam under test is the $j_m^{th}$ beam, the desired partial derivative is $$\frac{\partial B}{\partial a_{j_m}^{(k)}} = 2\sum_{i \in D} (h_i^{(k)} - d_i) F_{ij_m}$$

disregarding the weights $w_i$.

In 57, the change in the cost function is calculated by the product $$\Delta B = \frac{\partial B}{\partial a_{j_m}^{(k)}} \Delta a^{(k)}$$

which is a first order approximation to the true change in the cost function.

In 58 a test for a negative Δφ is made. If the change in the cost function is negative, the grain is accepted in 59 by letting the new value of the $j_m^{th}$ beam fluence become $(a_{j_m}^{(k)} + \Delta a^{(k)})$. Also at 59, the summations $$h_i^{(k)} = \sum_j F_{ij} a_j^{(k)}$$

are updated for each value of i by letting the new value of $h_i^{(k)}$ become $(h_i^{(k)} + F_{ij_m} \Delta a^{(k)})$ and the PTV cost B is updated to (B+ΔB).

If the change in cost was found to be positive at 58 or after updating the beam fluence, doses and cost in 59, the iteration counter is incremented by 1 and the grain magnitude is decremented in 60. The grain magnitude decreases in some predetermined manner as the iterations proceed, so that it becomes a small number towards the end of the procedure.

A test is made in 61 to see whether the wanted number of iterations has been completed. If the answer is negative, the process continues in 54. Otherwise, the SA procedure on the PTV is completed and the computer program exits at 62. This PTV optimization can be carried out with a fixed number of iterations since the important changes occur in the first 20 or 30 tests for each of the beam fluences.

Figure 6:
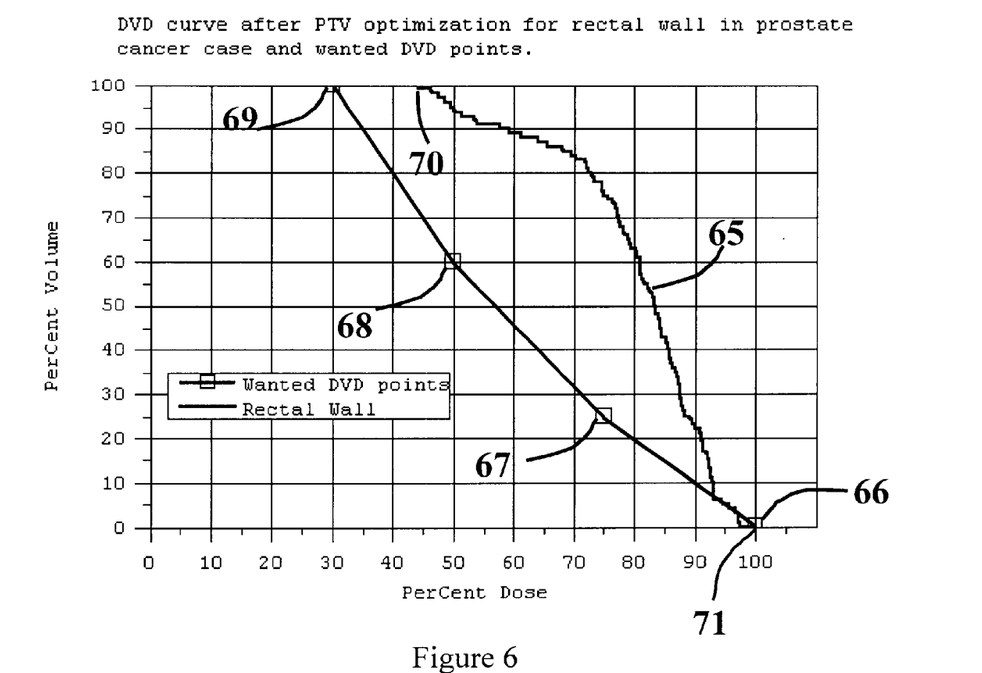
FIG. 6 shows DVDs to be used in illustrating the step of CALCULATE OAR DVDS AND CALCULATE DESIRED DOSES $s_i$ IN OAR'S in FIG. 3.

FIG. 6 will be used to demonstrate the methodology developed to allow the therapist to define several points in the DVD curve for the OAR, as indicative of the desired dose-volume constraints in the optimization, and use those points to calculate the desired doses $s_i$ in each of the voxels of the corresponding OAR. The assignment of doses $s_i$ for the rectal wall in a prostate cancer case similar to that of FIG. 1 will be described as the example to be used henceforth. The PTV and OARs were simulated in a computer code and the dose matrix F was calculated using a public domain X-ray beam simulation program. A stack of eleven planes containing a prostate, a rectal wall and a bladder wall were simulated. The DVD curve 65 corresponds to the results of a PTV only optimization, obtained by the procedure described in FIG. 5. Points 66, 67, 68 and 69 correspond to 4 points in the DVD desired by the therapist to be the result of the fall optimization of the prostate case. The dose assignment is carried out by a number of steps that can best be described with reference to the example of FIG. 6. The procedure is based on the observed fact that the OAR voxels that receive the highest dose after the PTV only optimization are approximately the same voxels that will receive the highest dose after a fall ASA optimization. The steps are described as:

1—After the PTV only optimization, all the voxels in the OAR are ranked in increasing order of dose. The voxel number i corresponding to the minimum dose at 70 will be the first voxel in the ranking, at 44% dose. The voxel number corresponding to the maximum dose at 71 will be the last voxel in the ranking, at 100% dose. Let us assume that the total number of voxels in the OAR is $N_v$.

2—Starting at the high dose end, the desired DVD is separated into $(N_s-1)$ sections, where $N_s$ is the number of points prescribed by the therapist. Section 1 is between points 66 and 67. Section 2 is between points 67 and 68 and Section 3 is between points 68 and 69.

3—Operating on Section 1:
  a) Point 66 corresponds to a volume of 0% and a dose of 100%. Point 67 corresponds to a volume of 25% and a dose of 75%. That indicates that it is desired that 25%-0%=25% volume in the OAR has to receive doses between 75% and 100%.
  b) The number of voxels that are to fall in Section 1 is then given by $0.25N_v$.
  c) Starting with the ranked dose values with 100% dose and moving towards those with lower doses, $0.25N_v$ voxels are picked, their ranked doses scaled to the interval between 75% and 100% and the resulting scaled doses are assigned to the desired doses $s_i$ for that group of voxels.

4—Operating on Section 2:
  a) Point 67 corresponds to a volume of 25% and a dose of 75%. Point 68 corresponds to a volume of 60% and a dose of 50%. That indicates that it is desired that 60%-25%=35% volume in the OAR has to receive doses between 50% and 75%.
  b) The number of voxels that are to fall in Section 2 is then given by $0.35N_v$.
  c) Starting from the highest unassigned ranked dose values and moving towards those with lower doses, $0.35N_v$ voxels are picked, their ranked doses scaled to the interval between 50% and 75% and the resulting scaled doses are assigned to the desired doses $s_i$ for that group of voxels.

5—Operations on Section 3 are similar to those of Section 2, with the voxel with minimum dose at 70 being the last assigned voxel with a desired dose of 30% at 69.

Figure 7:
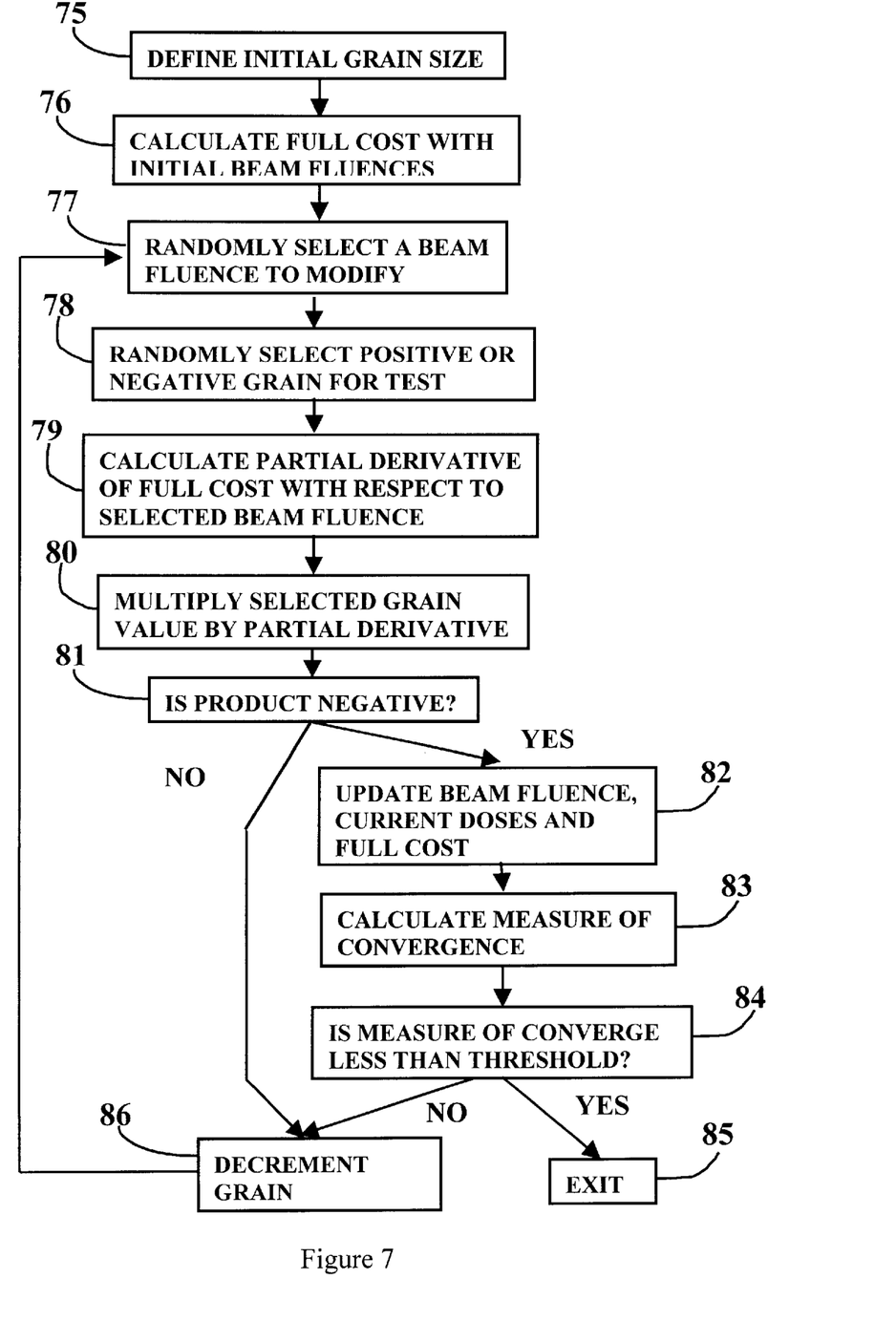
FIG. 7 is a diagram that describes the flow and processing of information in the OPTIMIZE PTV AND OARs step in FIG. 3.

FIG. 7 describes the part of the Adaptive Simulated Annealing procedure that carries out the full optimization, including all the therapist's constraints. There is a substantial similarity with the operations described in FIG. 5, but the cost and change in cost calculations now include the OAR terms and their dynamic characteristics. A measure of convergence has now been incorporated in order to decide when the iterative procedure can be stopped. There are several possibilities: the cost function decreases at a rate slower than a certain threshold, the average dose in all the OARs decreases at a rate slower than another threshold, the root-mean-square error in the PTV dose decreases at a rate slower than still another threshold, and others. No specific measure is described for the preferred embodiment of the invention.

The initial magnitude of the grain, $\Delta a^{(0)}$, is taken in 75 as a fixed fraction of the largest beam fluence resulting from the PTV only optimization described in FIG. 5.

In 76, the fall cost function $$B(a) = \sum_{i \in D} w_i \Phi(h_i^{(k)}, d_i) + \sum_{\substack{i \in S \\ (h_i^{(k)} - s_i) > 0}} \beta_i \Theta(h_i^{(k)}, s_i)$$

is calculated.

For the analytic quadratic cost function described above, the full cost function becomes $$B(a) = \sum_{i \in D} w_i \left( \sum_j h_i^{(k)} - d_i \right)^2 + \sum_{\substack{i \in S \\ (\sum_j h_i^{(k)} - s_i) > 0}} \beta_i \left( \sum_j h_i^{(k)} - s_i \right)^2$$

The initial beam fluence values used for this calculation can be those obtained from the PTV only optimization. The desired PTV doses $d_i$ were prescribed by the therapist and the desired OAR doses $s_i$ are obtained by the method described in conjunction with FIG. 6.

In 77, a random number generator is used to select one of the beams j for a test. In 78, a positive or negative sign for the grain is chosen at random for the test corresponding to the current iteration.

In 79, the first partial derivative of the fall cost function with respect to the beam being tested is calculated. For example, for the above quadratic and if the beam under test is the $j_m^{th}$ beam, the desired partial derivative is $$\frac{\partial B}{\partial a_{j_m}^{(k)}} = 2 w_i \sum_i (h_i^{(k)} - d_i) F_{ij_m} + 2\beta_i \sum_{\substack{i \in S \\ (\sum_j h_i^{(k)} - s_i) > 0}} (h_i^{(k)} - s_i) F_{ij_m}$$

In 80, the change in the cost function is calculated by the product $$\Delta B = \frac{\partial B}{\partial a_{j_m}^{(k)}} \Delta a^{(k)}.$$

In 81, a test for a negative $\Delta B$ is made. If the change in the cost function is negative, the grain is accepted in 82 by letting the new value of the $j_m^{th}$ beam fluence become $(a_{j_m}^{(k)} + \Delta a^{(k)})$. Also at 82, the summations $$h_i^{(k)} = \sum_j F_{ij} a_j^{(k)}$$

are updated for each value of i by letting the new value of $h_i^{(k)}$ become $(h_i^{(k)} + F_{ij_m} \Delta a^{(k)})$ and the full cost B is updated to $(B + \Delta B)$.

If the change in cost was found to be positive in 81 or after updating the beam fluence, doses and cost in 82, the chosen measure of convergence is calculated in 83. The measure of convergence is tested by comparison with the desired threshold at 84. If the measure is smaller than the threshold, the process exits at 85. If the measure is not smaller than the threshold or the value of $\Delta B$ was found to be non-negative at 81, the grain magnitude is decreased in some predetermined manner at 86 and the process continues at 77.

Safeguards as a total maximum number of iterations, tests for divergence and other tests can be implemented to guard against malfunction, but they are not a part of the invention.

Figure 8:
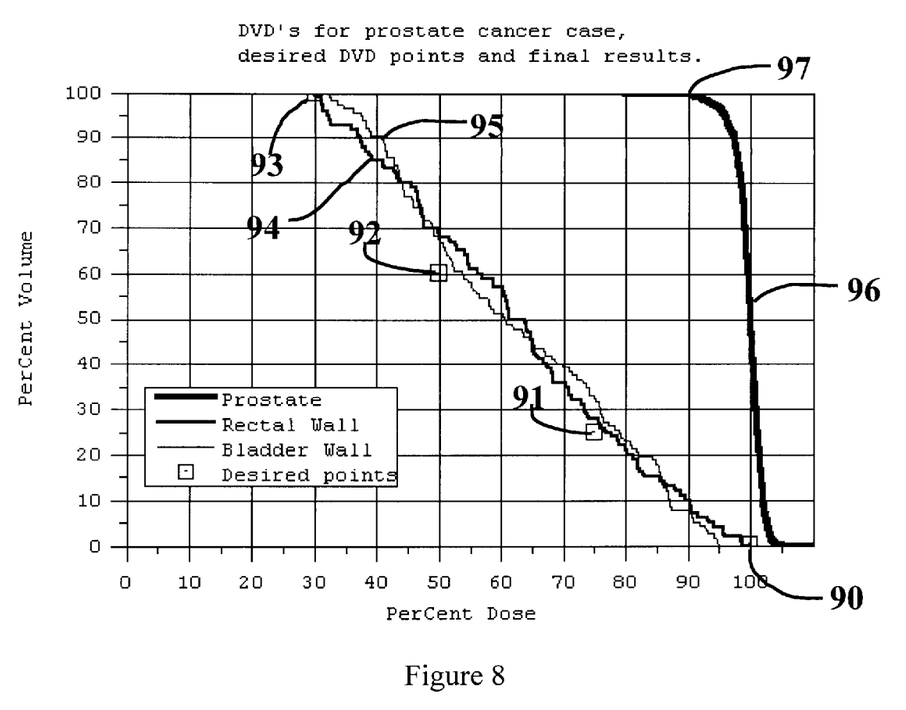
FIG. 8 shows DVDs resulting from the optimization of a hypothetical prostate cancer case.

FIG. 8 shows the DVDs resulting from a full optimization of the simulated prostate cancer case discussed in conjunction with FIG. 6. The points at 90, 91, 92 and 93 correspond to the therapist's specification for the two OARs (rectal wall and bladder wall). The curve 94 corresponds to the resulting DVD for the rectal wall and the curve 95 is the resulting DVD for the bladder wall. Comparison of curves 94 and 95 with points 90, 91, 92 and 93 shows that the ASA algorithm has succeeded in optimizing the problem to a degree close to the therapist's specifications. Curve 96 is the DVD for the PTV, which shows a minimum dose of 90% at 97, an acceptable value for this type of patient case. The weight parameters $\beta_i$ were set equal to 1.0 for the optimization. Giving higher weight to the OAR cost terms results results in a closer fit between the resulting DVDs and the therapist's specification at the expense of having a lower minimum dose in the PTV, which would most certainly not be acceptable.

I claim:

1. A method of radiation treatment planning for flux modulated radiation treatment or flux modulated radiation surgery enabling the production of a desirable radiation dose distribution from a predetermined number and arrangement of pencil beams, said method comprising the steps of:
   a. calculating the desired doses in each of the voxels of each organ at risk from the results of a preliminary optimization of the planning treatment volume and from desired points in the dose volume distributions for each organ at risk, and
   b. calculating the optimum fluences for said pencil beams by minimizing an adaptive analytic cost function of the desired dose in the voxels in said planning treatment volume and of said desired doses in each of the voxels in organs at risk by the method of simulated annealing, whereby a therapist can specify the desired dose in the voxels of said planning treatment volume and said desired points in the dose volume distributions for each organ at risk and take advantage of the fast computational possibilities with analytic cost functions for substantial improvements in clinical performance of a treatment planning system.

2. The method of treatment planning according to claim 1, wherein the step of calculating desired the doses in each of the voxels of each organ at risk is carried out by scaling the doses received by each of said voxels in a preliminary optimization of the planning treatment volume to the range of doses desired for said voxels.

3. The method of treatment planning according to claim 1, wherein the step of calculating the desired doses in each of the voxels of each organ at risk includes:
   a. ranking of said voxels in each organ at risk in order of the dose received as a result of a preliminary optimization of said planning treatment volume,
   b. defining sections in a dose volume distribution for each organ at risk delimited by points provided by a therapist,
   c. calculating how many voxels belong in each of said sections and which range of doses correspond to each of said sections from said points provided by a therapist,
   d. picking voxels to be assigned to each of said sections from said ranking so that those voxels that received more dose as a result of said preliminary optimization will also receive more dose in the dose volume distribution formed from said points provided by a therapist, and
   e. scaling the doses received by each of said voxels as a result of said preliminary optimization to the dose range in its corresponding section.

4. The method of treatment planning according to claim 1, wherein the step of calculating the optimum fluences includes the minimization of a cost function of the form $$B(a) = \sum_{i \in D} w_i \Phi(h_i^{(k)}, d_i) + \sum_{\substack{i \in S \\ (h_i^{(k)} - s_i) > 0}} \beta_i \Theta(h_i^{(k)}, s_i)$$

wherein
- a=vector of pencil beam fluences
- $h_i^{(k)}$ is the dose received by voxel i at iteration k,
- $d_i$=desired dose in voxel i of the PTV,
- D=the region that includes all the voxels of the PTV,
- $s_i$=desired dose in voxel i of the OAR,
- S=the region that includes all the voxels of the OAR,
- $\Phi()$=an analytic function of the dose received by voxel i in the PTV at iteration k and of the desired dose for the same voxel,
- $\Theta()$=an analytic function of the dose received by voxel i in the OAR at iteration k and of the desired dose for the same voxel,
- $w_i$=weights that determine how closely the minimization of $\Phi()$ has to be carried for voxel i in the PTV,
- $\beta_i$=weights that determine how closely the minimization of $\Theta()$ has to be carried for voxel i in the OAR, The dose received by a voxel i at iteration k is obtained by $$h_i^{(k)} = \sum_j F_{ij} a_j^{(k)}$$

wherein:
- $a_j^{(k)}$=fluence for the $j^{th}$ pencil beam at iteration k and
- $F_{ij}$=element of the dose matrix F, giving the dose received in voxel i per unit fluence of pencil beam j.

5. The method of treatment planning according to claim 4, wherein the analytic function $\Phi()$ is a function of the difference between its arguments $$\Phi(h_i^{(k)}, d_i) = \Phi(h_i^{(k)} - d_i).$$

6. The method of treatment planning according to claim 4, wherein the analytic function $\Theta()$ is a function of the difference between its arguments $$\Theta(h_i^{(k)}, s_i) = \Theta(h_i^{(k)} - s_i).$$

7. The method of treatment planning according to claim 4, wherein the analytic function $\Phi()$ is the quadratic function $$\Phi(h_i^{(k)}, d_i) = (h_i^{(k)} - d_i)^2.$$

8. The method of treatment planning according to claim 4, wherein the analytic function $\Theta()$ is the quadratic function $$\Theta(h_i^{(k)}, s_i) = (h_i^{(k)} - s_i)^2.$$

9. An apparatus for optimizing the process of radiation treatment planning for flux modulated radiation treatment or flux modulated radiation surgery enabling the production of a desirable radiation dose distribution from a predetermined number and arrangement of pencil beams, involving computer techniques comprising:
  a. means for calculating the desired doses in each of the voxels of each organ at risk from the results of a preliminary optimization of the planning treatment volume and from desired points in the dose volume distributions for each organ at risk, and
  b. means for calculating the optimum fluences for said pencil beams by minimizing an adaptive analytic cost function of the desired dose in the voxels in said planning treatment volume and of said desired doses in each of the voxels in organs at risk by the method of simulated annealing, whereby a therapist can specify the desired dose in all the voxels of said planning treatment volume and said desired points in the dose volume distributions for said organs at risk and take advantage of the fast computational possibilities with analytic cost functions for substantial improvements in clinical performance of a treatment planning system.

10. The apparatus of claim 9 wherein said means for calculating desired the doses in each of the voxels of each organ at risk allows the scaling of the doses received by each of said voxels in a preliminary optimization of the planning treatment volume to the range of doses desired for said voxels.

11. The apparatus of claim 9, wherein said means for calculating the desired doses in each of the voxels of each organ at risk includes:
  a. means for ranking of said voxels in each organ at risk in order of the dose received as a result of a preliminary optimization of said planning treatment volume,
  f. means for defining sections in a dose volume distribution for each organ at risk delimited by points provided by a therapist,
  g. means for calculating how many voxels belong in each of said sections and which range of doses correspond to each of said sections from said points provided by a therapist,
  h. means for picking voxels to be assigned to each of said sections from said ranking so that those voxels that received more dose as a result of said preliminary optimization will also receive more dose in the dose volume distribution formed from said points provided by a therapist, and
  i. means for scaling the doses received by each of said voxels as a result of said preliminary optimization to the dose range in its corresponding section.

12. The apparatus of claim 9, wherein said means for calculating the optimum fluences includes means for the minimization of a cost function of the form $$B(a) = \sum_{i \in D} w_i \Phi(h_i^{(k)}, d_i) + \sum_{\substack{i \in S \\ (h_i^{(k)} - s_i) > 0}} \beta_i \Theta(h_i^{(k)}, s_i)$$

wherein
- a=vector of pencil beam fluences
- $h_i^{(k)}$ is the dose received by voxel i at iteration k,
- $d_i$=desired dose in voxel i of the PTV,
- D=the region that includes all the voxels of the PTV,
- $s_i$=desired dose in voxel i of the OAR,
- S=the region that includes all the voxels of the OAR,
- $\Phi()$=an analytic function of the dose received by voxel i in the PTV at iteration k and of the desired dose for the same voxel,
- $\Theta()$=an analytic function of the dose received by voxel i in the OAR at iteration k and of the desired dose for the same voxel,
- $w_i$=weights that determine how closely the minimization of $\Phi()$ has to be carried for voxel i in the PTV, $\beta_i$=weights that determine how closely the minimization of $\Theta(\ )$ has to be carried for voxel i in the OAR, The dose received by a voxel i at iteration k is defined by $$h_i^{(k)} = \sum_j F_{ij} a_j^{(k)}$$

wherein:

$a_j^{(k)}$=fluence for the $j^{th}$ pencil beam at iteration k and $F_{ij}$=element of the dose matrix F, giving the dose received in voxel i per unit fluence of pencil beam j.

13. The means of claim 12, wherein the analytic function $\Phi(\ )$ is a function of the difference between its arguments $$\Phi(h_i^{(k)}, d_i) = \Phi(h_i^{(k)} - d_i).$$

14. The means of claim 12, wherein the analytic function $\Theta(\ )$ is a function of the difference between its arguments $$\Theta(h_i^{(k)}, s_i) = \Theta(h_i^{(k)} - s_i).$$

15. The means of claim 12, wherein the analytic function $\Phi(\ )$ is the quadratic function $$\Phi(h_i^{(k)}, d_i) = (h_i^{(k)} - d_i)^2.$$

16. The means of claim 12, wherein the analytic function $\Theta(\ )$ is the quadratic function $$\Theta(h_i^{(k)}, s_i) = (h_i^{(k)} - s_i)^2.$$

* * * * *